United States Patent [19]

Szycher et al.

[11] Patent Number: 4,638,043
[45] Date of Patent: * Jan. 20, 1987

[54] DRUG RELEASE SYSTEM

[75] Inventors: Michael Szycher, Lynnfield; Donald J. Dempsey, Newbury; Jonathan L. Rolfe, North Easton, all of Mass.

[73] Assignee: Thermedics, Inc., Woburn, Mass.

[*] Notice: The portion of the term of this patent subsequent to Sep. 30, 2003 has been disclaimed.

[21] Appl. No.: 768,623

[22] Filed: Aug. 23, 1985

Related U.S. Application Data

[63] Continuation-in-part of Ser. No. 670,810, Nov. 13, 1984.

[51] Int. Cl.[4] .................. C08G 18/10; A61F 13/00
[52] U.S. Cl. .................................. 528/75; 522/6; 522/44; 522/46; 604/304; 604/372; 424/28; 424/32
[58] Field of Search ............... 528/75; 204/159.14, 204/159.19; 604/304, 372; 424/28, 32; 522/6, 44, 46

[56] References Cited

U.S. PATENT DOCUMENTS

| | | | |
|---|---|---|---|
| 3,062,210 | 11/1962 | Scholl | 128/156 |
| 3,342,183 | 9/1967 | Edenbaum | 128/268 |
| 3,374,134 | 3/1968 | Waldman | 156/239 |
| 3,526,224 | 9/1970 | Potts | 128/156 |
| 3,567,119 | 3/1971 | Wilbert et al. | 239/6 |
| 3,570,482 | 3/1971 | Emoto et al. | 128/156 |
| 3,598,122 | 8/1971 | Zaffaroni | 128/268 |
| 3,598,123 | 8/1971 | Zaffaroni | 128/268 |
| 3,731,683 | 5/1973 | Zaffaroni | 128/268 |
| 3,734,097 | 5/1973 | Zaffaroni | 128/268 |
| 3,742,951 | 7/1973 | Zaffaroni | 128/268 |
| 3,842,832 | 10/1974 | Wideman et al. | 128/169 |
| 3,870,593 | 3/1975 | Elton et al. | 161/159 |
| 3,881,473 | 5/1975 | Corvi et al. | 128/90 |
| 3,975,567 | 8/1976 | Lock | 428/315 |
| 4,034,751 | 7/1977 | Hung | 128/156 |
| 4,038,239 | 7/1977 | Coyner et al. | 528/75 |
| 4,144,317 | 3/1979 | Higuchi et al. | 424/21 |
| 4,156,067 | 5/1979 | Gould | 528/73 |
| 4,189,467 | 2/1980 | von Bittera et al. | 424/14 |
| 4,209,605 | 6/1980 | Hoy et al. | 528/54 |
| 4,215,684 | 8/1980 | Westip | 128/156 |
| 4,233,969 | 11/1980 | Lock et al. | 128/156 |
| 4,236,550 | 12/1980 | Braun et al. | 139/421 |
| 4,306,551 | 12/1981 | Hymes et al. | 128/156 |
| 4,307,717 | 12/1981 | Hymes et al. | 128/156 |
| 4,321,117 | 3/1982 | Kaetsu et al. | 521/28 |
| 4,331,135 | 5/1982 | Westip | 128/156 |
| 4,336,243 | 6/1982 | Sanvordeker | 424/28 |
| 4,340,043 | 7/1982 | Seymour | 128/132 |
| 4,391,106 | 7/1983 | Schafer et al. | 66/193 |
| 4,411,754 | 10/1983 | Kaetsu et al. | 424/78 |
| 4,447,590 | 3/1984 | Szycher | 528/76 |
| 4,460,369 | 7/1984 | Seymour | 604/897 |
| 4,476,697 | 10/1984 | Schafer et al. | 66/193 |
| 4,483,759 | 11/1984 | Szycher et al. | 528/76 |
| 4,496,535 | 1/1985 | Gould et al. | 424/19 |

FOREIGN PATENT DOCUMENTS 273966 10/1974 Australia .

Primary Examiner—John Kight
Assistant Examiner—Nathan M. Nutter
Attorney, Agent, or Firm—Pahl, Lorusso & Loud

[57] ABSTRACT

A drug releasing system in the form of a medical patch comprised of a drug dispensing polyurethane member as a matrix for a therapeutically effective amount of drug dispersed therein. The polyurethane of the drug dispensing or releasing member is a polyurethane acrylic copolymer which is the reaction product of an oligomer of a diisocyanate, a glycol with a molecular weight between the range of 500–5,000 molecular weight units and an acrylyl chain terminator having a molecular weight between the range of 40–200 molecular weight units cured by actinic radiation. In its preferred embodiment, the foregoing drug releasing or dispensing member is incorporated into a medical patch or drug release system comprised of successive layers of an ultrathin polyurethane substrate, pressure sensitive adhesive, the above-described drug releasing member and optionally a second layer of adhesive.

The drug release system of the present invention is biocompatible, oxygen and water vapor permeable, flexible and can incorporate a wide variety of drugs for a controlled, sustained release to the wearer.

26 Claims, 3 Drawing Figures

DRUG RELEASE SYSTEM

CROSS-REFERENCE TO RELATED APPLICATION

This application is a continuation-in-part application of prior application U.S. Ser. No. 670,810, filed Nov. 13, 1984, entitled "Drug Dispensing Wound Dressing".

BACKGROUND OF THE INVENTION

There has long been a need for a drug release system which is soft, pliable and elastic, oxygen and water vapor permeable, translucent, yet high in tensile strength and abrasion resistance, biocompatible and which can release a wide variety of drugs in a controlled, sustained manner.

A drug release system or medical patch can be a transdermal patch or transdermal drug release system for use on intact skin for therapeutic effects not necessarily in the area on which such a system is applied. An example is the release of Nitroglycerine from such a release system applied on the skin of the chest for the treatment of Angina Pectoris.

A drug release system or medical patch may also be a wound dressing for delivery of drugs to a specific site to topically treat a local wound. Sustained release of drugs directly to a wound site provides long lasting therapeutic action without the danger of toxic side effects that can occur with systemic drug delivery (by injection or capsule). Systemic antibiotics, for example, must be administered within four hours of wounding, when circulation is still optimal. If treatment is delayed, conditions for bacterial growth will develop, and complete curing would be more difficult. Once an infection is established, it becomes difficult to systemically administer certain antibiotics for extended periods at levels that are safe, yet still effective at the wound site. Drugs administered systemically, rather than applied locally, are distributed throughout the body; thus, the amount of drugs actually reaching the target is only a small part of the total dosage. This problem is further compounded in the trauma patient by shock, which decreases vascular flow to the tissue.

In addition, a drug release system or medical patch can be used for prosthetic devices within the body. If used as a prosthetic device, the most significant criteria for the material is that it be biocompatible. That is, the material should not induce the formation of a thrombus which can embolize into the peripheral bloodstream.

Although there are now on the market dressing "skin patches" that contain a few specific drugs such as nitroglycerine and scopolamine, a system is needed which can deliver many drugs never before encapsulated in a patch. Since most drug compounds are highly sensitive to environmental influences, they can be chemically damaged by a thermal curing process or organic solvents.

At present, the most commercially successful burn and superficial skin wound dressing is a polyether-based polyurethane, moisture-vapor permeable membrane compounded with silica gel. The composition, known as "Op-Site" ®, described in U.S. Pat. Nos. 4,340,043 and 4,460,369 assigned to Smith & Nephew Ltd., is in the form of a thin film having a surface coated with a polyvinylethylether adhesive. This material, however, still suffers from the inability to incorporate biologically active agents such as coagulants and antibiotics into the membrane, rather than into the adhesive, and from difficulty in formation and application as a bandage which conforms to the contour of the site of application.

It has now been discovered that the variety of drugs which can be incorporated into the medical patch can be widened by the use of a specific light-cured rather than heat-cured polyurethane in the drug releasing layer or member as a matrix for a therapeutically effective amount of drug dispersed therein.

SUMMARY OF THE INVENTION

The present invention is a drug release system or medical patch formed of a drug releasing member with a therapeutically effective amount of drug dispersed therein. In the preferred embodiment of the invention, the drug releasing or dispensing member is incorporated into a medical patch comprised of successive layers of a substrate of an ultrathin polyurethane membrane, a pressure sensitive adhesive, and the drug releasing member described above. The patch may optionally incorporate another layer of pressure sensitive adhesive on the skin-contacting side of the drug releasing member.

It is therefore an object of the present invention to provide a drug release system for prosthetic devices or for placement over intact or wounded skin which physically incorporates drugs such as steroids, antibiotics, birth control drugs, cardiovascular drugs, chemotherapeutic agents, analgesics, antimicrobials, coagulants, local anesthetics and anti-inflammatories into the dressing structure having appreciable tensile strength rather than into the adhesive or thin coating on the dressing so that the drugs are released in a controlled, sustained manner.

Still a further object of the present invention is to provide a drug release system which can incorporate a wide variety of drugs which were not able to be incorporated into prior art systems.

Yet a further object of the invention is to provide a system which incorporates a layer of polymeric material which is liquid at room temperature and which has sufficiently low viscosity at room temperature (prior to cure) to facilitate admixture with a drug to form a homogeneous blend.

Still a further object of the invention is to provide such a system being capable of curing at room temperature without release of heat (non-exothermic).

It is a further object of the present invention to provide such a system which is strong yet flexible, translucent and capable of oxygen and water vapor transmission.

It is a still further object of the present invention to provide a material for use as a drug release system which is nontoxic, non-carcinogenic and biocompatible.

The foregoing and other objects and features of the claimed invention will be understood by those skilled in the art from a reading of the description which follows.

DESCRIPTION OF THE PREFERRED EMBODIMENTS

Figure 1:
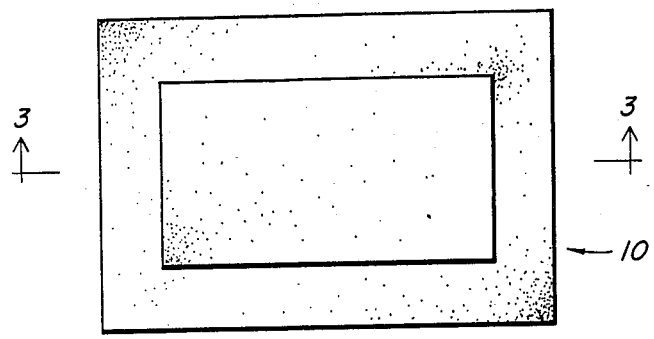
FIG. 1 is a plan view of the drug release system or medical patch of the present invention.
Figure 2:
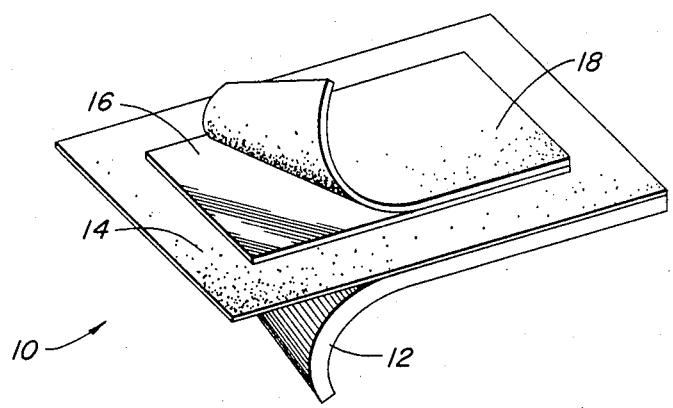
FIG. 2 is an exploded view of the various layers of the medical patch.
Figure 3:
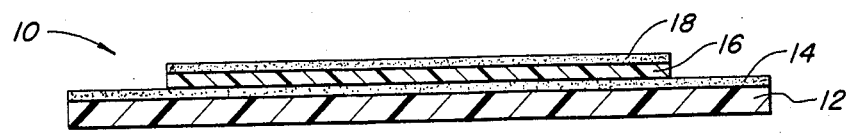
FIG. 3 is a cross-sectional view of the patch of FIG. 1, taken along the cut at line 3—3.

At the outset, the invention is described in its broadest overall aspects with a more detailed description following.

It is intended that the drug release system or medical patch of the present invention be capable of use as a prosthetic device and for use over both intact and wounded skin. For example, it can be used over intact skin as a transdermal delivery system. Over broken or traumatized skin, the system is used as a medicated wound dressing. Over burned skin, the system is a medicated burn dressing which can clean as well as medicate the skin. In addition, the system can be formed as a medicated implantable prosthesis. The term "medical patch", therefore, is intended to cover all these uses.

The drug release system of the present invention is comprised of a drug dispensing or releasing member containing a therapeutically effective amount of drug dispersed therein. The member is comprised of a polyurethane formed from an oligomer which is cured by actinic radiation with the drug doped therein. The ability to cure without release of heat is a particularly important characteristic of the oligomer because many drugs are heat labile and the drug embodied in this oligomer must remain active after curing to the polymer. The cured oligomer or polyurethane must also be capable of releasing the drug in a controlled, sustained manner so that it elutes out at a therapeutically beneficial rate. The oligomer must not contain water or solvents, which hinder the effectiveness of many drugs and it must cure to a completely cured polymer, leaving no sites available to react with the drug. The cured oligomer or polyurethane should be flexible so that it can be made to conform to the site of the contact to the wearer. In addition, when the system contacts the skin of the wearer, it must breath, i.e. be oxygen and water vapor permeable, and be biocompatible.

This oligomer is the reaction product of (1) a diisocyanate, (2) a glycol having a molecular weight between the range of 500-5,000 molecular weight units; and (3) an acrylyl chain terminator having a molecular weight between the range of 40-200 molecular weight units. In addition to the foregoing required constituents, the composition preferably includes a catalyst and photosensitizer and, optionally, an antioxidant and a surfactant. The resulting oligomer comprises two diisocyanate units for each glycol unit and has only one acrylic group terminator at each end of the polyurethane chain. This polyurethane and the process to formulate it is further described in U.S. Pat. No. 4,483,759 entitled "Actinic Radiation Cured Polyurethane Acrylic Copolymer" issued on Nov. 20, 1984 to Michael Szycher et al, the teachings of which are incorporated herein by reference. Before the reaction product is cured, however, a therapeutically effective amount of the chosen drug or drugs is incorporated into the composition. The total amount of drug added is generally 1-10 weight % of the oligomer.

The drug chosen for incorporation into the above oligomer composition, of course, depends on the condition to be treated. Steroids, antibiotics, antimicrobials, local anesthetics, vasodilators, coagulants, antifungals, birth control drugs, cardiovascular drugs, analgesics, chemotherapeutic agents and anti-inflammatories, as well as a mixture of one or more, can be successfully compounded into this oligomer.

Also blended into the oligomer with the drugs may be hydrophilic plasticizers and/or drug carriers such as propylene glycol, polyethylene glycol of varying molecular weights, glycerine and other similar compounds to make the cured film softer and to solvate and to aid the transport of the drug out of the polymer matrix and into the skin. The composition of oligomer and drug and optionally the plasticizers and/or drug carriers is then cured as disclosed in U.S. Pat. No. 4,483,759.

Because the curing process proceeds by exposure to actinic light, most preferably ultraviolet light, a wide variety of drugs can be incorporated into the drug releasing system of the present invention at any point within the formulation/reaction sequence. The process does not involve any exothermic reaction and, therefore, no cooling of any reaction mixture is required prior to the addition of a drug having activity highly susceptible to degradation by heat. However, it is preferred that the drug be added to the uncured liquid, vinyl-terminated oligomer as the last additive prior to curing and after aeration for removal of all entrained gases. Stated another way, any drug that functions in its intended manner after exposure to actinic radiation is operable in the present drug release system. For reasons which follow, the drug also must be water soluble.

The cured polyurethane product or drug releasing member is crystal clear, biocompatible, soft and elastomeric and serves to release the incorporated drug in a controlled, sustained manner while protecting the portion of the incorporated drug yet to be released. The cured polyurethane is a solid and contains the selected drug dispersed throughout the polyurethane. Since the polyurethane of the drug releasing member is somewhat hydrophilic, it absorbs water vapor evaporating from the skin of the wearer. As the water vapor permeates through the polyurethane, it condenses to water and dissolves the drug. The flow of the drug to the wearer of the medical patch proceeds in a controlled sustained manner because of the concentration differential. That is, the drug will flow out of the polyurethane where there is a high concentration of the drug and into the skin where there is a low concentration of the drug. In addition, the release is controlled by the size of the molecular pores which are formed in the polyurethane.

Referring to the drawing, the preferred embodiment of the drug release system of the present invention is a medical patch 10 comprising successive layers of an oxygen and water vapor permeable polyurethane substrate 12, a pressure sensitive adhesive 14, and the above-described drug releasing member 16. The medical patch may optionally be provided with a second layer of adhesive 18 on the exposed side of the drug releasing member should it be desired that the system stick to the site on which it is placed.

The substrate layer 12 of the present invention provides support for the remaining layers and allows for the transmission of oxygen and water vapor but not of dirt or liquid water which would serve as a growth medium for bacteria. The layer can be anisotropic by which is meant that the material stretches more in one direction than in the other and resembles the stretching characteristics of human skin. The substrate should be flexible so that it conforms to the contour of the site of application.

A polyurethane material which is biocompatible is desirable because it can be made to exhibit the listed properties. Generally, the polyurethane used for this layer is the reaction product of a diisocyanate and a macroglycol, which results in an isocyanate terminated prepolymer. The prepolymer is then reacted with a chain terminator to form a vinyl terminated polyurethane oligomer. Optionally, a photosensitizer may be admixed with the foregoing compounds at any point prior to curing to form a homogeneous admixture. The admixture is then treated to set the oligomer into a solid polyurethane film. This is generally done by heat or light. As used in this specification, the term "macroglycol" has reference to any glycol having a molecular weight in excess of 500 molecular weight units. Any polyurethane having the above described properties can be used for the substrate layer of this invention.

For example, a suitable product for use in this layer of the system is TECOFLEX ®, a tradename of Thermo Electron Corporation for a polyurethane which is the reaction product of (1) dicyclohexyl methane diisocyanate, (2) a polytetramethylene ether polyol having a molecular weight in the range 1000–3000 and (3) 1,4-butane diol and is further described in U.S. Pat. No. 4,523,005 entitled "Extrudable Polyurethane for Prosthetic Devices Prepared from a Diisocyanate, a Polytetramethylene Ether Polyol and 1,4-butane diol", in the name of Michael Szycher. The teachings of this patent are incorporated herein by reference.

Another product which can be used in this layer is SPANDRA ™, a tradename of Thermedics Inc. for a polyurethane which is the reaction product of (1) isophorone diisocyanate, (2) a macroglycol having a molecular weight in the range of 500–5000 molecular weight units, and (3) a chain terminator containing hydroxyl and vinyl groups and is further described in U.S. application Ser. No. 726,809, entitled "Anisotropic Wound Dressing" filed Apr. 25, 1985 in the name of Michael Szycher et al. The teachings of this application are incorporated herein by reference. This oligomer is cured by exposure to ultraviolet light to form a solid polyurethane film.

Another product which can be used in this layer is a polyurethane polymer which is the reaction product of (1) dicyclohexyl methane diisocyanate, (2) a polytetramethylene ether polyol having a molecular weight in the range of 1000–2000 and (3) 1,4-butane diol, wherein for each diol there are two dicyclohexyl methane diisocyanates and one glycol, the average molecular weight of the polymer is 120,000 molecular weight units and a weight average molecular weight of 315,000 molecular weight units. This polyurethane polymer is further described in U.S. Pat. No. 4,447,590, in the name of Michael Szycher, the teachings of which are incorporated herein by reference.

Another suitable polyurethane is a crosslinked, thermoplastic aliphatic polyurethane which is the reaction product of (1) isophorone diisocyanate, (2) a polycarbonate glycol having a molecular weight of 500–2000 molecular weight units and having the following formula:

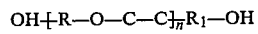

where R and $R_1$ are aliphatic linear chains of 1–20 carbons, (3) an acrylic compound having both hydroxyl and vinyl functional groups which is preferably an acrylic compound such as hydroxyethyl acrylate or hydroxyethyl methacrylate and (4) an acrylic crosslinker. The composition may optionally include an antioxidant and a polyurethane catalyst. The composition of liquid oligomer is treated with heat, preferably infrared light, to activate the crosslinker, which in turn thermosets the polyurethane and forms a solid polyurethane film.

Another suitable polyurethane is the reaction product of (1) an aliphatic diisocyanate selected from the group consisting of hexamethylene diisocyanate, isophorone diisocyanate, trimethyl hexamethylene diisocyanate, dicyclohexyl methane diisocyanate, and dimer acid diisocyanate, (2) cyclohexane dimethanol and (3) a poly tetra methylene ether polyol having a molecular weight in the range of 500–5000 molecular weight units, the resulting polymer having a molecular weight between the range of 80–120 thousand molecular weight units, as set forth in U.S. Pat. No. 4,131,604 in the name of Michael Szycher, the teachings of which are incorporated herein by reference.

Also suitable for use is the polyurethane formed in the drug release system described above and set forth in U.S. Pat. No. 4,483,759 to Michael Szycher et al. The oligomer is formed and cured to a polyurethane film without incorporation of the drug for use in this substrate layer.

An open mesh knitted fabric may optionally be used within the polyurethane of this layer as a reinforcement. The knitted reinforcing fabric, if used, should be an anisotropic fabric formed with a basic stitch construction to create equally spaced and sized hexagonal interstices. The geometry of the construction gives this fabric its anisotropic characteristics. In turn, the presence of the fabric in the polyurethane will enable the layer to be thin yet anisotropic and strong. It will not wrinkle easily and will hold its shape so it is easily applied. A suitable fabric is sold by Gehrring Textiles, New York, N.Y., and is formed of Nylon 6-6 yarns. The fabrics described in copending application U.S. application Ser. No. 726,809 are suitable for this purpose. The relevant teachings of that application are incorporated herein by reference.

The polyurethane chosen for this substrate layer is prepared and cured as described in the respective patent or application. A thin layer is formed to create the substrate for the medical patch.

A thin continuous layer of adhesive 14 is applied to the fully cured and prepared substrate layer, with or without the fabric reinforcement, in a conventional manner. Any pressure-sensitive adhesive conventionally used for wound dressings or bandages may be spread over the layer, e.g. a polyacrylate adhesive or a polyvinylethyl ether blend adhesive.

The drug releasing member 16, as described above, is then applied to the adhesive 14 by setting it thereon.

A second layer of adhesive 18 may optionally be applied to the exposed side of the drug releasing member 16. As well as making the medical patch ready for application to a person, this second adhesive layer could be used for debridement on burn patients, in which removal of the medical patch removes the dead burned skin and cleans the wound.

A release paper or plastic film (not shown) is then applied over the entire exposed adhesive surfaces, 14 and 18, of the medical patch in a conventional manner.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A drug releasing member for incorporation into a medical patch comprised of a drug dispensing polyurethane having a therapeutically effective amount of a drug or drugs dispersed therein and capable of being released in a sustained manner, said polyurethane consisting essentially of the reaction product of:
   (a) a diisocyanate;
   (b) a glycol having a number average molecular weight between the range of 500–5000 molecular weight units; and
   (c) an acrylyl chain terminator having a number average molecular weight between the range of 40–200 molecular weight units; and wherein there are 2 diisocyanate units for each glycol unit, and there is only one acrylyl group terminator at each end of the polyurethane chain.

2. The member of claim 1 wherein said drug or drugs dispersed within said polyurethane comprises 1–10 wt. % of said polyurethane.

3. The member of claim 1 wherein said drug or drugs dispersed within said polyurethane is selected from the group consisting of steroids, coagulants, antibiotics, birth control drugs, chemotherapeutic agents, cardiovascular drugs, analgesics, antifungals, topical anesthetics, anti-inflammatories, antimicrobials and vasodilators.

4. The member of claim 1 further comprising a hydrophylic plasticizer mixed into said polyurethane.

5. The member of claim 1 further comprising a drug carrier mixed into said polyurethane.

6. A process for forming a drug releasing member for incorporation into a medical patch comprising:
   (A) providing reactants consisting essentially of:
       (1) a diisocyanate;
       (2) a glycol having a number average molecular weight between the range of 500–5000 molecular weight units; and
       (3) an acrylyl chain terminator having a number average molecular weight between the range of 40–200 molecular weight units; and
   wherein the proportions of reactants are provided so that there are two diisocyanate units for each glycol unit, and there is only one acrylyl group terminator at each end of the oligomer formed from the reactants;
   (B) mixing the reactants in the presence of
       (1) a catalyst capable of catalyzing urethane bond formation; and
       (2) a photosensitizer
   to form an oligomer;
   (C) degassing the oligomer to remove the entrained air;
   (D) adding a therapeutically effective amount of a desired drug or drugs; and
   (E) actinic radiation curing the mixture of oligomer and drug or drugs to form a drug releasing member.

7. The process of claim 6 wherein in step (E) actinic radiation comprises ultraviolet light.

8. The process of claim 6 wherein in step (A) the diisocyanate is aliphatic.

9. The process of claim 6 wherein the catalyst is dioctyl tin dilaurate.

10. The process of claim 6 wherein in step (D) the drug or drugs is selected from the group consisting of steroids, coagulants, birth control drugs, cardiovascular drugs, chemotherapeutic agents, analgesics, antibiotics, antifungals, topical anesthetics, anti-inflammatories, antimicrobials and vasodilators.

11. The process of claim 6 wherein in step (D) said drug or drugs dispersed in said oligomer comprises 1–10 wt. % of said oligomer.

12. A medical patch comprising:
    a substrate layer;
    a first layer of pressure sensitive adhesive on one side of the substrate layer; and
    a drug releasing member adhered to said first layer of pressure sensitive adhesive comprising a drug dispensing polyurethane containing a therapeutically effective amount of a drug or drugs dispersed therein.

13. The medical patch of claim 12 further comprising a second layer of pressure sensitive adhesive on the exposed side of the drug releasing member.

14. The medical patch of claim 12 wherein the substrate layer is comprised of a polyurethane consisting essentially of the reaction product of
    (1) a diisocyanate;
    (2) a glycol having a number average molecular weight between the range of 500–5000 molecular weight units; and
    (3) an acrylyl chain terminator having a number average molecular weight between the range of 40–200 molecular weight units; and
wherein there are 2 diisocyanate units for each glycol unit; and there is only one acrylyl group terminator at each end of the polyurethane chain; and
wherein said reaction product is cured by actinic radiation to form the polyurethane.

15. The medical patch of claim 12 wherein the substrate layer is comprised of a polyurethane which is the reaction product of
    (1) dicyclohexyl methane diisocyanate;
    (2) a polytetramethylene ether polyol having a number average molecular weight between the range of 1000–3000 molecular weight units; and
    (3) 1,4-butane diol.

16. The medical patch of claim 12 wherein the substrate layer is comprised of a polyurethane which is the reaction product of
    (1) isophorone diisocyanate;
    (2) a macroglycol having a number average molecular weight in the range of 500–5000 molecular weight units; and
    (3) a chain terminator containing hydroxyl and vinyl groups; and
wherein said reaction product is cured by ultraviolet radiation to form the polyurethane.

17. The medical patch of claim 12 wherein the substrate layer is comprised of a polyurethane which is the reaction product of
    (1) dicyclohexyl methane diisocyanate;
    (2) a polytetramethylene ether polyol having a number average molecular weight in the range of 1000–2000 molecular weight units; and
    (3) 1,4-butane diol, wherein for each diol there are two dicyclohexyl methane diisocyanates and one glycol; and
the number average molecular weight of the polymer is 120,000 units and a weight average molecular weight of 315,000 molecular weight units.

18. The medical patch of claim 12 wherein the substrate layer is comprised of a thermoplastic, aliphatic polyurethane which is the reaction product of
   (1) isophorone diisocyanate;
   (2) a polycarbonate glycol having an average molecular weight in the range of 500-2000 molecular weight units; and
   (3) a chain terminator having both hydroxyl and vinyl functional groups.

19. The medical patch of claim 12 wherein the substrate layer is comprised of a polyurethane elastomer which is the reaction product of
   (1) an aliphatic diisocyanate selected from the group consisting of hexamethylene diisocyanate, isophorone diisocyanate, trimethyl hexamethylene diisocyanate, dicyclohexyl methane diisocyanate, and dimer acid diisocyanate;
   (2) cyclohexane dimethanol; and
   (3) a poly tetra methylene ether polyol having a number average molecular weight in the range of 500-5000 molecular weight units, the resulting polymer having a number average molecular weight between the range of 80-120 thousand molecular weight units.

20. The medical patch of claim 12 wherein the drug releasing member layer is comprised of a polyurethane which is the reaction product of
   (1) a diisocyanate;
   (2) a glycol having a number average molecular weight between the range of 500-5000 molecular weight units; and
   (3) an acrylyl chain terminator having a number average molecular weight between the range of 40-200 molecular weight units; and
   wherein there are 2 diisocyanate units for each glycol unit; and
   there is only one acrylyl group terminator at each end of the polyurethane chain;
   and wherein the reactants are mixed to form a reactive mixture and degassed to remove entrained air and after which is added a therapeutically effective amount of a desired drug or drugs, and said composition of oligomer and drug is exposed to actinic radiation curing to form the drug releasing member layer.

21. The medical patch of claim 20 wherein in said drug releasing member layer, said drug or drugs comprises between 1-10 wt. % based on the weight of said polyurethane.

22. The medical patch of claim 20 wherein in said drug releasing member layer, said drug or drugs is selected from the group consisting of steroids, coagulants, antibiotics, antifungals, topical anesthetics, birth control drugs, cardiovascular drugs, analgesics, chemotherapeutic agents, anti-inflammatories, antimicrobials and vasodilators.

23. The medical patch of claim 22 wherein said polyurethane further comprises a hydrophylic plasticizer to aid transport of the drug to the wearer.

24. The medical patch of claim 22 wherein said polyurethane further comprises a drug carrier to aid transport of the drug to the wearer.

25. The medical patch of claim 12 wherein the drug releasing member is smaller in area than the substrate layer.

26. A polyurethane oligomer consisting essentially of:
   (a) a diisocyanate;
   (b) a glycol having a number average molecular weight between the range of 500-5000 molecular weight units; and
   (c) an acrylyl chain terminator having a number average molecular weight between the range of 40-200 molecular weight units; wherein there are 2 diisocyanate units for each glycol unit; and there is only one acrylyl group terminator at each end of the polyurethane chain.

* * * * *